United States Patent [19]

Kratoska et al.

[11] Patent Number: 5,445,616
[45] Date of Patent: Aug. 29, 1995

[54] MEDICATION DELIVERY DEVICE AND METHOD OF CONSTRUCTION

[75] Inventors: Paul S. Kratoska, Brooklyn Park; Raymond F. McMullen, Shorewood, both of Minn.

[73] Assignee: Medtronic, Inc., Minneapolis, Minn.

[21] Appl. No.: 235,038

[22] Filed: Apr. 29, 1994

[51] Int. Cl.⁶ .................................. A61M 5/152
[52] U.S. Cl. .......................... 604/141; 604/891.1
[58] Field of Search ............ 604/141, 153, 891.1; 128/DIG. 12

[56] References Cited

U.S. PATENT DOCUMENTS

| | | | |
|---|---|---|---|
| 3,468,308 | 9/1969 | Bierman | 604/141 |
| 3,951,147 | 4/1976 | Tucker et al. | 604/891.1 |
| 4,193,397 | 3/1980 | Tucker et al. | 128/207.19 |
| 4,221,219 | 9/1980 | Tucker | 604/141 |
| 4,360,019 | 11/1982 | Portner et al. | 128/213 R |
| 4,692,147 | 9/1987 | Duggan | 604/93 |
| 4,886,499 | 12/1989 | Cirelli et al. | 604/141 |
| 4,978,338 | 12/1990 | Melsky et al. | 604/93 |
| 5,061,242 | 10/1991 | Sampson | 604/141 |
| 5,090,963 | 2/1992 | Gross et al. | 604/141 |
| 5,147,310 | 9/1992 | Giannini et al. | 604/141 |
| 5,176,644 | 1/1993 | Srisathapat et al. | 604/141 |
| 5,197,322 | 3/1993 | Indravudh | 604/141 |
| 5,242,406 | 9/1993 | Gross et al. | 604/141 |

*Primary Examiner*—Paul J. Hirsch
*Attorney, Agent, or Firm*—Curtis D. Kinghorn; Harold R. Patton

[57] ABSTRACT

A medication delivery device having a particularly compact size. The compact size is achieved by arranging the components of the device so that the reservoir refill port is positioned laterally adjacent a bellows medication reservoir. Preferably, the medication reservoir is doughnut shaped and the refill port is positioned in a centrally located aperture.

18 Claims, 2 Drawing Sheets

MEDICATION DELIVERY DEVICE AND METHOD OF CONSTRUCTION

FIELD OF THE INVENTION

The present invention relates to medication delivery devices which are implanted within the body of a patient and methods of construction of the devices. More particularly, the invention relates to a medication delivery device having a uniquely compact size due to the lateral placement of the fluid medication reservoir and the reservoir refill assembly and methods of its construction.

BACKGROUND OF THE INVENTION

The use of implantable fluid medication dispensers is well known. These devices typically include a medication reservoir within a generally cylindrically shaped housing. Some form of fluid flow control is also provided to control or regulate the flow of fluid medication from the reservoir to the outlet of the device for delivery of the medication to the desired location, usually through a catheter. The flow control may be provided by a pumping or metering device such as disclosed in U.S. Pat. No. 4,692,147 issued to Duggan. Other forms of flow control are disclosed in U.S. Pat. Nos. 3,951,147 and 4,360,019.

All implantable fluid medication dispensers must also include some means to replenish the fluid medication in the medication reservoir. The previously mentioned U.S. Pat. Nos. 4,692,147 to Duggan and 3,951,147 to Tucker et al. disclose typical reservoir refill assemblies. Both include an opening or port through which a resealable septum may be accessed. To refill the reservoir a hypodermic needle is inserted through the septum and into a chamber between the septum and a needle stop, which may be a plug or filter. The medication is injected under pressure into the chamber and flows into the Reservoir.

A disadvantage of these reservoir refill assemblies is that they have been stacked on top of the reservoirs. Thus, the external housing of the device must be sized not only to accommodate the depth of the reservoir but, additionally, the depth of the refill assembly including the septum, the chamber and the needle stop. This adds considerably to the total depth of the drug dispensing device which is undesirable, especially in view of technological advances being made in the miniaturization of other components of the device. Since the device is implanted in the body it is advantageous to make the device as small as possible. A smaller (thinner) device can be implanted in smaller people and in children and allows all patients to be more active.

SUMMARY OF THE INVENTION

The present invention is a medication delivery device having a particularly compact size. Specifically, a very thin profile is achieved by arranging the components of the device so that the medication reservoir is radially or laterally spaced from the reservoir refill assembly rather than being axially spaced or in a stacked relationship. The invention includes the method of making the device.

In one embodiment the invention is a medication delivery device comprising a housing, a reservoir within the housing, and a reservoir refill port or assembly in fluid communication with the reservoir. The refill assembly is substantially surrounded by the reservoir and is radially spaced from the reservoir in a lateral arrangement. The device includes an outlet port, and means connected between the reservoir and the outlet port for dispensing medication from the reservoir through the outlet port. The dispensing means may be a flow regulator or a flow restrictor. The reservoir may include an aperture through which the refill assembly is positioned. The aperture may be approximately concentric with a longitudinal axis of the housing.

In another embodiment the invention is a medication delivery device comprising a housing within which is a reservoir having an aperture approximately concentric with a longitudinal axis of the housing. A reservoir refill assembly is positioned within the aperture of the reservoir in fluid communication with the reservoir. A flow regulator is connected between the reservoir and an outlet port.

In a further embodiment the invention is a medication delivery device having a cover and a bulkhead connected to the cover. The bulkhead includes a base portion and a reservoir refill assembly which extends through the cover. The device further includes a reservoir having a top portion, a side portion, and a bottom portion. An aperture extends through the reservoir between the top and bottom portions. The bottom portion of the reservoir is connected to the base portion of the bulkhead such that the refill assembly extends through the aperture and is radially spaced from the reservoir in a lateral arrangement. A manifold is connected to the base portion of the bulkhead. The device further includes means for providing fluid flow from the refill assembly to the reservoir, a flow regulator in fluid communication with the reservoir, and an outlet port connected to the flow regulator. The refill assembly may include a hollow neck portion having first and second open ends, a resealable septum within the hollow neck portion near the first end thereof, a filter within the hollow neck portion near the second end thereof, and a refill chamber lying between the septum and the filter. Additionally, the manifold may include an inlet portion for receiving medication passing through the filter, and one or more fluid channels for carrying fluid from the inlet portion. The bulkhead may include one or more fluid flow paths for providing a fluid path from the one or more fluid channels of the manifold to the reservoir. The inlet portion and the one or more fluid channels of the manifold together with the one or more fluid flow paths of the bulkhead may comprise the means for providing fluid flow.

In another aspect, the invention is a method of making a medication delivery device. The method comprises providing a housing and mounting a reservoir within the housing. A reservoir refill port or assembly is mounted at least partially within the housing such that it is substantially surrounded by the reservoir and is radially spaced from the reservoir in a laterally positioned arrangement. The method further includes providing a fluid path between the reservoir refill assembly and the reservoir, providing an outlet port, and connecting between the reservoir and the outlet port a means for dispensing medication from the reservoir to the outlet port. The dispensing means may comprise a flow regulator. Further, the reservoir may include an aperture through which is positioned the reservoir refill assembly. In that aspect, the aperture may be approximately concentric with a longitudinal axis of the housing.

In a further embodiment the method of making the medication delivery device includes providing a housing and mounting a reservoir within the housing. The reservoir may have an aperture approximately concentric with a longitudinal axis of the housing. The method further includes mounting a reservoir refill assembly within the aperture of the reservoir so that the refill assembly is radially spaced from the reservoir in a laterally positioned arrangement and is in fluid communication with the reservoir. The method includes connecting a flow regulator to the reservoir, and connecting an outlet port to the flow regulator.

In another embodiment the invention is a method of making a medication delivery device comprising providing a cover and connecting a bulkhead to the cover. The bulkhead may include a base portion and a reservoir refill assembly extending at least partially through the cover. The method includes mounting a reservoir between the cover and the bulkhead, the reservoir having a top portion, a side portion, an aperture and a bottom portion. The bottom portion of the reservoir is connected to the base portion of the bulkhead such that the refill assembly is radially spaced from the reservoir in a lateral arrangement. The method further includes connecting a manifold to the base portion of the bulkhead, connecting between the reservoir and the refill assembly a means for providing fluid flow from the refill assembly to the reservoir, connecting a flow regulator in fluid communication with the reservoir, and connecting an outlet port to the flow regulator. The refill assembly may include a hollow neck portion having first and second open ends, a resealable septum within the hollow neck portion near the first end thereof, a filter within the hollow neck portion near the second end thereof, and a refill chamber lying between the septum and the filter. The manifold may include an inlet portion for receiving medication passing through the filter, and one or more fluid channels for carrying fluid from the inlet portion. The bulkhead may include one or more fluid flow paths for providing a fluid path from the one or more fluid channels of the manifold to the reservoir. Further, the inlet portion and the one or more fluid channels of the manifold together with the one or more fluid flow paths of the bulkhead may comprise the means for providing fluid flow.

DESCRIPTION OF THE PREFERRED EMBODIMENTS

Figure 1:
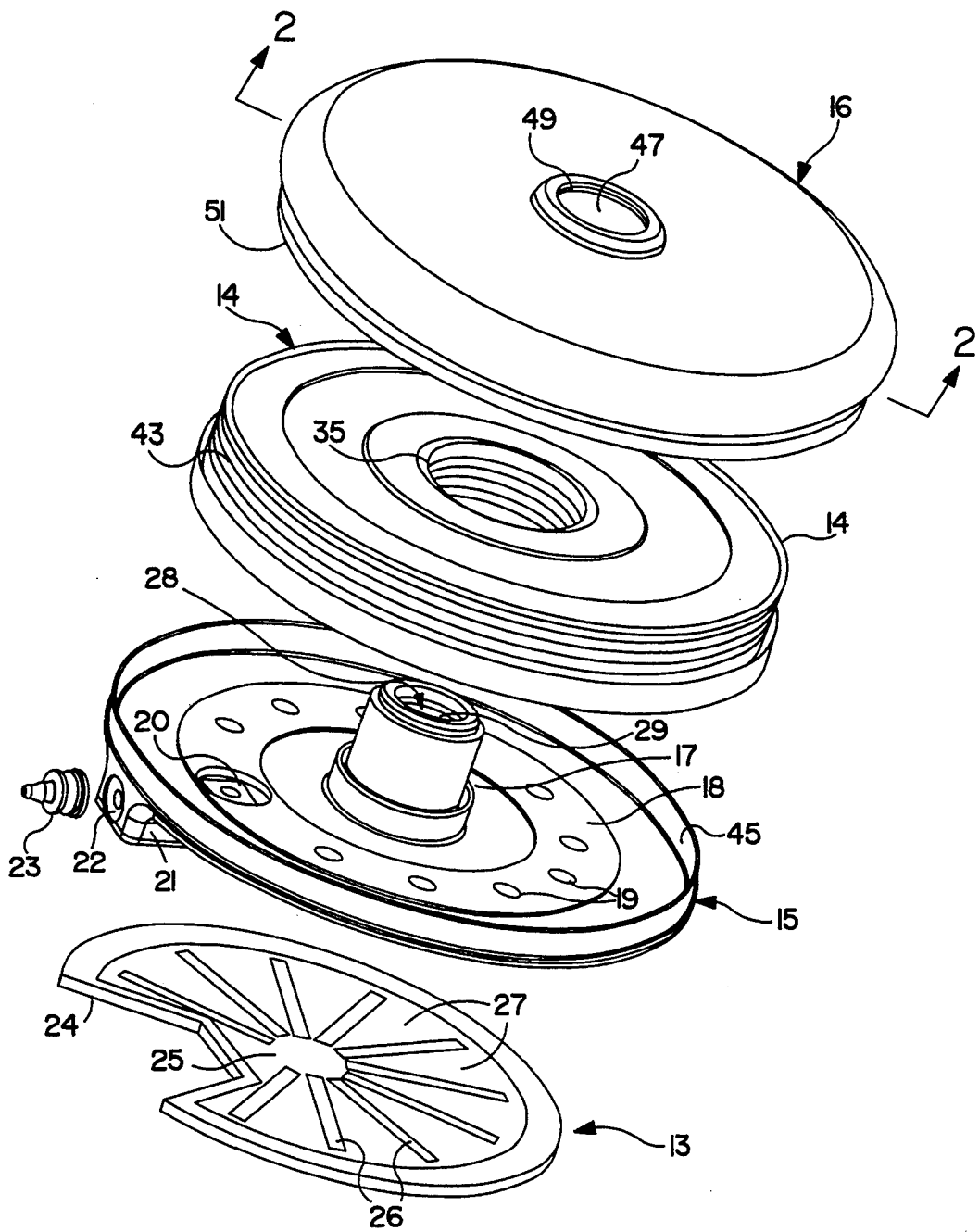
FIG. 1 is an exploded perspective view of one embodiment of the medication delivery device 10 of the present invention.
Figure 2:
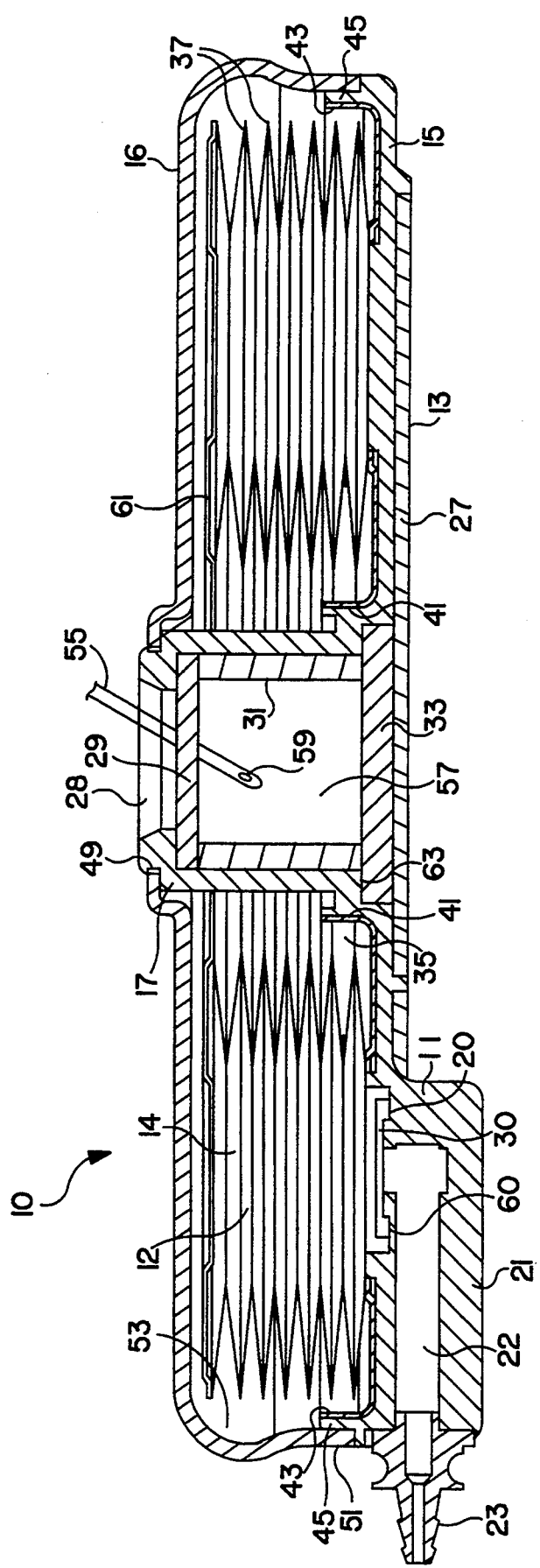
FIG. 2 is a cross-sectional view thereof, taken generally along line 2—2 of FIG. 1.

Referring now to FIGS. 1-2, a medication delivery device 10, for delivering a fluid medication 12, is illustrated. The term "medication" is used in its broad sense, and may be any fluid, whether or not the fluid is medicinal in nature. The term "fluid" is also used in its broad sense, and includes both liquids and gasses.

Turning again to FIGS. 1-2, the medication delivery device 10 may comprise five main components, namely, a manifold 13, a donut-shaped bellows reservoir 14, a bulkhead 15, a cover 16, and a flow regulator 30. Optionally, flow regulator 30 may be any type of flow restriction device such as capillary tubing. Additionally, it should be understood that although the embodiment of the invention disclosed in FIGS. 1 and 2 has a dispensing means consisting of a flow regulator, the invention is equally applicable to devices utilizing other means of dispensing medication such as programmable or nonprogrammable pumping means as will be familiar to those of skill in the art. The manifold 13, the reservoir 14, the cover 16, and the flow regulator 30 may all be bonded or assembled to the bulkhead 15 in any suitable way, as will be described in more detail below. The cover 16, manifold 13 and bulkhead 15 together form an external housing of the medication delivery device.

The bulkhead 15 may have a hollow neck 17, a base 18, a number of through holes 19, a flow regulator mounting cavity 20; an outlet housing 21, an outlet conduit 22, and an outlet port 23. Although ten through holes 19 are illustrated in FIG. 1, there may be fewer, or more, through holes 19.

Although the bulkhead 15's neck 17, base 18 and outlet housing 21 are illustrated as being made as one integral component, they may be manufactured as separate components, and then bonded or assembled together in any suitable way. Similarly, although the outlet port 23 is illustrated as being made as a separate component, which is then bonded or assembled to the outlet housing 21, the outlet port 23 and the outlet housing 21 may be made as one integral component.

Although not illustrated, for clarity, the medication delivery device 10 may be equipped with any suitable means for preventing back flow of any fluid into the outlet port 23, such as a check valve. The means for preventing back flow of any fluid into the medication delivery device 10's outlet port 23 may be mounted in any suitable location, either internally or externally of the device 10, such as in its outlet conduit 22 or adjacent to its outlet port 23.

Although also not illustrated, for clarity, the medication delivery device 10 may be equipped with any suitable means for permitting or preventing flow of the medication 12 out of the outlet port 23, such as an on-off valve. The means for permitting or preventing flow of the medication 12 out of the outlet port 23 may be mounted in any suitable location, either internally or externally of the device 10, such as in its outlet conduit 22 or adjacent to its outlet port 23.

The bulkhead 15's hollow neck 17 may have an inlet 28. Housed within the neck 17 may be a septum 29, which may be held in place by any suitable means, such as by a threaded hollow plug 31 or by an interference (press) fit between the neck 17 and the plug 31, or by welding the neck 17 to the plug 31. The septum 29 may be made from any suitable resilient, self-sealing material which may be pierced by a needle, such as silicone rubber. Neck 17, inlet 28 and septum 29 together comprise a refill port which enables reservoir 14 to be filled and refilled with medication in a manner described more fully hereafter.

Also housed within the neck 17 may be any suitable filter 33, which may be bonded or assembled within the neck 17 in any suitable way. For example, as seen in FIG. 2, the filter 33 may be held within the neck 17 by being sandwiched between the neck 17's shoulder 63 and the manifold 13's ribs 27.

The filter 33 may be selected to filter particles from the medication 12 of a size which might clog, or otherwise harm, any of the device 10's components which are located downstream from the filter 33; or which might clog, or otherwise harm, whatever is receiving the medication 12 from the device 10. For example, if the device 10 is to be used for medical or veterinary purposes, the filter 33 may be selected to filter out particles as small as bacteria, or even as small as viruses, to help protect the patient or animal from the possibility of infection. By way of further example, if the filter 33 is located upstream from the fluid flow regulator 30, then the filter 33 may serve the dual functions of filtering out harmful bacterial or viruses from the medication 12, and of filtering out any particles from the medication 12 which might clog, or otherwise harm, the fluid flow regulator 30 and/or flow restrictor and keep it from operating properly.

Although the filter 33 is illustrated as being located within the bulkhead 15's neck 17, it could be placed in any other suitable location within the medication delivery device 10 which is upstream from where the outlet port 23 exits the device 10, such as in the reservoir 14, the through holes 19, the manifold 13's inlet recess 25, the manifold 13's outlet channels 26, the flow regulator mounting cavity 20, the outlet conduit 22, or the outlet port 23. Alternatively, the filter 33 may be placed externally of the medication delivery device 10 in any suitable location, such as upstream from the neck 17's inlet port 28, or downstream from the device 10's outlet port 23. In such an event, the neck 17's shoulder 63 may be eliminated, since it would no longer be needed to hold the filter 33 in place within the neck 17.

The flow regulator 30 may be bonded or assembled to the bulkhead 15's regulator mounting cavity 20, over the outlet conduit 22, in any suitable way. Alternatively, the flow regulator 30 may be placed within the device 10 in any other suitable location which is downstream from the reservoir 14, the outlet conduit 22, or the outlet port 23.

Alternatively, the flow regulator 30 may be placed externally of the medication delivery device 10 in any suitable location, such as downstream of the outlet port 23. In such an event, the flow regulator mounting cavity 20 may be eliminated.

The flow regulator 30 may be any suitable fluid flow regulator which is selected to have the particular fluid flow characteristics which are desired for the particular intended use of the medication delivery device 10. For example, in order to help prevent an overdose of medication from being delivered to a patient by the device 10, the flow regulator 30 may be selected to provide a predetermined maximum flow rate of the medication 12, despite an overpressure of the medication 12 within the reservoir 14 which exceeds the normal operating parameters of the device 10. Such an overpressure might occur if, for example, the reservoir 14 was overfilled with the medication 12.

The manifold 13 may be bonded or assembled to the periphery of the bottom of the bulkhead 15's base 18 in any suitable way, and may form the bottom of the medication delivery device 10. The manifold 13 may have a cutout 24, an inlet recess 25, a number of outlet channels 26, and a number of ribs 27. The cutout 24 may be sized to accommodate the bulkhead 15's outlet housing 21. The ribs 27 may separate the outlet channels 26 from each other, and may help to hold the filter 33 within the bulkhead 15's neck 17. One end of each of the outlet channels 26 may be in fluid communication with the inlet recess 25, while the other end of each of the outlet channels 26 may be in fluid communication with a respective through hole 19 in the bulkhead 15.

Although ten outlet channels 26 and nine ribs 27 are illustrated, there may be fewer, or more, outlet channels 26 and ribs 27. Although the manifold 13's inlet recess 25 and outlet channels 26 are illustrated as being separate components, the outlet channels 26 may be eliminated and replaced by an enlarged inlet recess 25 which fluidly communicates with the bulkhead 15's through holes 19; and the inlet recess 25 may be eliminated and replaced by enlarged outlet channels 26 which are in fluid communication with the bulkhead 15's hollow neck 17.

The reservoir 14 may have a central hole 35, pleated inner and outer sides 37, 39, and an open bottom having inner and outer mounting flanges 41, 43. The reservoir 14 may be bonded or assembled to the bulkhead 15 in any suitable way; such as by bonding or assembling its inner mounting flange 41 to the outside of the base of the neck 17, and by bonding or assembling its outer mounting flange 43 to the inside of the bulkhead 15's peripheral lip 45. As a result, the bulkhead 15's base 18 forms the bottom of the reservoir 14, and the medication 12 may enter the reservoir 14 through the holes 19 in the base 18.

The use of a donut-shaped reservoir 14, with the bulkhead 15's neck 17 extending through the reservoir 14's central hole 35, may be preferred. This is because such a construction results in an unusually compact medication delivery device 10 while retaining sufficient medication storage capacity. This arrangement provides a compact radially adjacent or side-by-side positioning of the reservoir and the refill port which does not add to the thickness of the medical delivery device in the direction of the longitudinal axis of the housing. Such compactness may be particularly desirable for the device 10 in certain circumstances, such as if it is designed to be implanted within a patient's body. Although the reservoir 14 and its central hole 35 are illustrated as having circular shapes, they could have any other suitable rounded or angular shape, such as oval, square or rectangular. Additionally, instead of being positioned concentrically with the longitudinal axis of the housing at the center of reservoir 14 as illustrated, hole 35 could be offset to any desired nonconcentric location.

The reservoir 14's pleated inner and outer sides 37, 39 permit the volume of the reservoir 14 to be varied. For example, as seen in FIG. 2, when the reservoir 14 is full, then its pleated inner and outer sides 37, 39 unfold a maximum amount, thereby permitting the reservoir 14's top 61 to be located a maximum distance from the bulkhead 15's base 18, which forms the bottom of the reservoir 14.

On the other hand, when the reservoir 14 is empty or evacuated, its pleated inner and outer sides 37, 39 fold up a maximum amount, thereby permitting the reservoir 14's top 61 to be located a minimum distance from the bulkhead 15's base 18.

Although the reservoir 14 is illustrated as having pleated inner and outer sides 37, 39, the reservoir 14 may be any other suitable adjustable volume device. For example, the reservoir 14 may be a simple balloon or bladder, having unpleated sides, which is made from any suitable flexible or elastic material, such as rubber or plastic.

The cover 16 may have a central hole 47 for the bulkhead 15's neck 17; and inner and outer mounting flanges 49, 51. The cover 16 may be bonded or assembled to the bulkhead 15 in any suitable way, such as by bonding or assembling its inner mounting flange 49 to the outside of the top of the neck 17, and by bonding or assembling its outer mounting flange 51 to the outside of the bulkhead 15's peripheral lip 45.

A positive pressure may be imparted to the medication 12 within the reservoir 14 in any suitable way. For example, the space 53 between the reservoir 14 and the cover 16 may be pressurized in any suitable way, such as by locating in the space 53 a quantity of any suitable, volatile substance which has a relatively high vapor pressure at the intended operating temperature range of the medication delivery device 10. The suitable, volatile substance may, for example, be Freon 87, which has a gas liquid-gas vapor pressure of 3.9 PSIG at 37° C. or R-11 which has a vapor pressure of 8.4 PSIG at 37° C. Alternatively, the space 53 may be pressurized by filling it with a compressed gas.

Alternatively, a positive pressure may be imparted to the medication 12 within the reservoir 14 by making the reservoir 14 to be self-collapsing, such as by fabricating the reservoir 14 from an elastic material which is stretched when the reservoir 14 is filled with the medication 12.

Alternatively, a positive pressure may be imparted to the medication 12 within the reservoir 14 by using an external mechanical force to collapse the reservoir 14, such as by locating a spring between the reservoir 14's top 61 and the inside of the cover 16.

The medication delivery device 10 may be initially filled with the medication 12 in any suitable way, such as by first inserting a hollow needle 55 through the neck 17's septum 29, and into the space 57 which is located between the septum 29 and the filter 33. Any undesired perforation of the filter 33 by the needle 55 may be prevented in any suitable way, such as by providing a space 57 between the septum 29 and the filter 33. In addition, the needle 55 may be selected to be of the type which has a relatively blunt end, with an outlet hole 59 on its side. Further, although not illustrated for clarity, a perforated needle stop may be located in the neck 17 between the septum 29 and the filter 33. The size of the perforations in the needle stop may be selected to be small enough to prevent the passage of the needle 55 therethrough; but large enough to permit the free passage of the medication 12 therethrough.

A vacuum may then applied to the needle 55 until all of the air in the space 57, the filter 33, the inlet recess 25, the outlet channels 26, the through holes 19, the reservoir 14, the flow regulator 30, the outlet conduit 22, and the outlet port 23 has been evacuated. The check valve, which was mentioned above, may be used to prevent air from flowing into the medication delivery device 10 through its outlet port 23 during the evacuation process. The needle 55 may then be withdrawn, and the septum 29 will automatically reseal itself, thereby not admitting any air into the device 10.

A new needle 55, connected to a source of medication 12, may then be inserted through the septum 29 into the space 57. The source of the medication 12 for the needle 55 may be pressurized. The medication 12 will then be drawn into and/or forced into the medication delivery device 10 through the needle 55, and fill the space 57, the filter 33, the inlet recess 25, the outlet channels 27, the through holes 19, the reservoir 14, the flow regulator 30, the outlet conduit 22, and the outlet port 23. After the medication delivery device 10 has been filled with the desired amount of the medication 12, the on-off valve, which was mentioned above, may be used to prevent the medication 12 from leaking out of the outlet port 23. The needle 55 may then be withdrawn, and the septum 29 will automatically reseal itself, to prevent any medication 12 from leaking out of, and any air from leaking into, the space 57.

Once the desired amount of the medication 12 has been inserted into the medication delivery device 10, any suitable delivery means, such as a catheter, may then be attached in any suitable way to the medication delivery device 10's outlet port 23, for conveying the medication 12 from the outlet port 23 to the location where the medication 12 is to be delivered. The on-off valve, which was mentioned above, may be turned on long enough to permit the medication 12 to flow out of the outlet port 23 until any undesired air in the outlet port 23 and the delivery means has been purged; at which time the on-off valve may then be turned off.

The medication delivery device 10 may then be secured in any suitable way in its location of intended use, such as by inserting it within a patient's body. The free end of the delivery means, such as the free end of the catheter, may then secured in any suitable way at the location where the medication 12 is to be delivered.

Once the device 10 and the free end of the delivery means have been secured in their desired location, the on-off valve may be turned on. That will permit the pressurized medication 12 in the reservoir 14 to flow out of the reservoir 14 and through the flow regulator 30, the outlet conduit 22, the outlet port 23, the delivery means. The rate of flow of the medication 12 from the reservoir 14 is governed by the flow regulator 30.

After a period of use, the reservoir 14 may be refilled with medication 12 in any suitable way, such as by the use of a needle 55 in a manner similar to that described above. Since the medication delivery device 10 may be installed within a patient's or animal's body, the needle 55 may be used to fill the reservoir 14 without removing the device 10 from the patient or animal, by simply inserting the needle 55 into the septum 29, through the patient's or animal's skin.

Within the scope of the present invention, the medication delivery device 10, as well as its various components, may have many alternative shapes, arrangements and variations. For example, instead of the device 10 having an overall circular or cylindrical shape, it could have any other suitable rounded or angular shape, such as oval, square or rectangular. In addition, instead of the device 10 having a concentric arrangement in which the bulkhead 15's neck 17 is located within the reservoir 14's hole 35, the reservoir 14 may not have a hole 35, and the neck 17 may be located along side of and substantially surrounded by the reservoir 14.

All of the medication delivery device 10's components may be made from, and bonded or assembled with, any suitable, durable, stable, corrosion-resistant substances which are compatible with the medication 12; which are compatible with the intended environment in which the device 10 is intended to be used; and which are compatible with the person, animal or thing with which the 10 is intended to be used.

The manifold 13; the cover 14; and the bulkhead 15's neck 17, base 18, outlet housing 21, outlet port 23 and plug 31 may be made from any suitable material which is also relatively rigid, such as plastic, ceramic, or metal. A suitable metal may be commercially pure titanium or Ti-6Al-4V.

The reservoir 14 may be made from any suitable material which is also relatively flexible (for proper operation of its pleated inner and outer sides 37, 39), such as plastic, or metal. A suitable metal may be commercially pure titanium or Ti-6Al-4V.

In addition, if the medication delivery device 10 is to be used in a medical or veterinary context, all of the device 10's components may be made from, and bonded or assembled with, substances which are compatible with at least one suitable sterilization process, such as heat sterilization (e.g., steam autoclaving), gas sterilization (e.g., ethylene oxide), liquid sterilization (e.g., hydrogen peroxide); or radiation sterilization (e.g., gamma radiation).

Any of the medication delivery device 10's components may be assembled together in any suitable leak-proof way, with or without gaskets, such as by using any suitable mechanical fastening means. For example, the plug 31 may be connected to the neck 17 with threads, in which case the septum 29 may act as a gasket for the plug 31. Further, the flow regulator 30 may be secured within the flow regulator mounting cavity 20 by the use of an 0-ring gasket and any suitable mechanical clamping mechanism.

In addition, any of the medication delivery device 10's components may also be bonded together in any suitable leak-proof way, such as by using any suitable welding process, such as laser welding. For example, the outer edge of the manifold 13 may be welded to the bottom of the periphery of the bulkhead 15's base 18; the outlet port 23 may be welded to the bulkhead 15's outlet housing 21; the reservoir 14's inner and outer mounting flanges 41, 43 may be welded to the bulkhead 15's neck 17 and lip 45, respectively; and the cover 16's inner and outer mounting flanges 49, 51 may be welded to the bulkhead 15's neck 17 and lip 45, respectively.

Alternatively, any of the medication delivery device 10's components may also be bonded together in a leak-proof way, with or without gaskets, by using any suitable bonding materials, such as adhesives, glues and epoxies.

Alternatively, any of the medication delivery device 10's components may be bonded together in a leak-proof way with any suitable anodic bonding process. For example, the flow regulator 30 may be anodically bonded to the regulator mounting cavity 20 if the flow regulator 30's base 11 and the regulator mounting cavity 20's bottom 60 are made from, or have applied thereto in any suitable way, any suitable respective materials which may be anodically bonded together, such as silicon or titanium and 7740 Pyrex ® glass made by the Corning Company of Corning, N.Y.

Alternatively, if the regulator's base 11 and the cavity's bottom 60 are not made from, or coated with, materials which may be anodically bonded directly together, then a layer of any suitable, compatible material which is anodically bondable with the regulator's base 11 and the cavity's bottom 60 may be inserted between the regulator's base 11 and the cavity's bottom 60 in any suitable way, before starting the anodic bonding process. For example, if both the regulator's base 11 and the cavity's bottom 60 were made from, or were coated with, 7740 Pyrex ® glass (which will not anodically bond to itself), then the layer of suitable, compatible, anodic bonding material may be selected to be made from silicon.

It is understood that the foregoing forms of the present invention were described and/or illustrated strictly by way of non-limiting example.

In view of all of the disclosures herein, these and further modifications, adaptations and variations of the present invention will now be apparent to those skilled in the art to which it pertains, within the scope of the following claims.

We claim:

1. A medication delivery device comprising:
   a housing,
   a reservoir within said housing,
   a reservoir refill port in fluid communication with said reservoir and positioned such that said reservoir refill port is laterally adjacent to said reservoir and substantially surrounded by said reservoir,
   an outlet port, and
   means connected between said reservoir and said outlet port for dispensing medication from said reservoir through said outlet port.

2. A device as in claim 1 wherein said dispensing means comprises a flow regulator.

3. A device as in claim 1 wherein said reservoir includes an aperture and wherein said refill port is positioned within said aperture.

4. A device as in claim 3 wherein said aperture is approximately concentric with a longitudinal axis of said housing.

5. A medication delivery device comprising:
   a housing,
   a reservoir within said housing, said reservoir having an aperture approximately concentric with a longitudinal axis of said housing,
   a reservoir refill port positioned within said aperture of said reservoir, said refill port being in fluid communication with said reservoir, said reservoir refill port positioned such that said reservoir refill port is laterally adjacent to said reservoir and substantially surrounded by said reservoir,
   a flow regulator connected to said reservoir, and
   an outlet port connected to said flow regulator.

6. A medication delivery device comprising:
   a cover,
   a bulkhead connected to said cover, said bulkhead including a base portion and a reservoir refill port extending through said cover,
   a reservoir including a top portion, a side portion, an aperture and a bottom portion, said bottom portion being connected to said base portion of said bulkhead such that said reservoir refill port is positioned laterally adjacent to said reservoir and extends through said aperture in said reservoir, said reservoir substantially surrounds said reservoir refill port,
   a manifold connected to said base portion of said bulkhead,
   means for providing fluid flow from said reservoir refill port to said reservoir,
   a flow regulator in fluid communication with said reservoir, and
   an outlet port connected to said flow regulator.

7. A medication delivery device as in claim 6 wherein said reservoir refill port includes:
   a hollow neck portion having first and second open ends,
   a resealable septum within said hollow neck portion near said first end thereof,
   a filter within said hollow neck portion near said second end thereof, and
   a refill port chamber lying between said septum and said filter.

8. A medication delivery device as in claim 7 wherein said manifold includes an inlet portion for receiving medication passing through said filter, and one or more fluid channels for carrying fluid from said inlet portion, and wherein said bulkhead includes one or more fluid flow paths for providing a fluid path from said one or more fluid channels of said manifold and said reservoir, and wherein said inlet portion and said one or more fluid channels of said manifold together with said one or more fluid flow paths of said bulkhead comprise said means for providing fluid flow.

9. A method of making a medication delivery device comprising:
providing a housing,
mounting a reservoir within said housing,
mounting a reservoir refill port at least partially within said housing, said reservoir refill port being positioned laterally adjacent to said reservoir and substantially surrounded by said reservoir,
providing a fluid path between said reservoir refill port and said reservoir,
providing an outlet port, and
connecting, between said reservoir and said outlet port, a means for dispensing medication from said reservoir to said outlet port.

10. The method of claim 9 wherein said dispensing means comprises a flow regulator.

11. The method of claim 9 further including providing said reservoir with an aperture and mounting said reservoir refill port within said aperture.

12. The method of claim 11 wherein said aperture provided is approximately concentric with a longitudinal axis of said housing.

13. A method of making a medication delivery device comprising:
providing a housing,
mounting a reservoir within said housing, said reservoir having an aperture approximately concentric with a longitudinal axis of said housing,
mounting a reservoir refill port within said aperture of said reservoir such that said refill port is positioned laterally adjacent said reservoir and is in fluid communication with said reservoir, said reservoir refill port being positioned substantially surrounded by said reservoir,
connecting a flow regulator to said reservoir, and
connecting an outlet port to said flow regulator.

14. A method of making a medication delivery device comprising:
providing a cover,
connecting a bulkhead to said cover, said bulkhead including a base portion and a reservoir refill port extending at least partially through said cover,
mounting a reservoir between said cover and said bulkhead, said reservoir having a top portion, a side portion, an aperture and a bottom portion,
connecting said bottom portion of said reservoir to said base portion of said bulkhead such that said refill port is positioned laterally adjacent to said reservoir and extends through said aperture in said reservoir, said refill port is positioned so that said reservoir substantially surrounds said refill port,
connecting a manifold to said base portion of said bulkhead,
connecting between said reservoir and said refill port a means for providing fluid flow from said refill port to said reservoir,
connecting a flow regulator in fluid communication with said reservoir, and
connecting an outlet port to said flow regulator.

15. The method of claim 14 wherein said refill port includes:
a hollow neck portion having first and second open ends,
a resealable septum within said hollow neck portion near said first end thereof,
a filter within said hollow neck portion near said second end thereof, and
a refill port chamber lying between said septum and said filter.

16. The method of claim 15 wherein said manifold includes an inlet portion for receiving medication passing through said filter, and one or more fluid channels for carrying fluid from said inlet portion, and wherein said bulkhead includes one or more fluid flow paths for providing a fluid path from said one or more fluid channels of said manifold and said reservoir, and wherein said inlet portion and said one or more fluid channels of said manifold together with said one or more fluid flow paths of said bulkhead comprise said means for providing fluid flow.

17. A medication delivery device comprising:
a cover;
a bulkhead connected to said cover, said bulkhead including a base portion and a reservoir refill port extending through said cover, said bulkhead further including one or more fluid flow paths for providing a fluid path from the one or more fluid channels of said manifold and said reservoir, said refill port including:
a hollow neck portion having first and second open ends,
a resealable septum within said hollow neck portion near said first end thereof,
a filter within said hollow neck portion near said second end thereof, and
a refill port chamber lying between said septum and said filter;
a reservoir including a top portion, a side portion, an aperture and a bottom portion, said bottom portion being connected to said base portion of said bulkhead such that said refill port is positioned laterally adjacent to said reservoir and extends through said aperture in said reservoir;
a manifold connected to said base portion of said bulkhead, said manifold including an inlet portion for receiving medication passing through said filter and one or more fluid channels for carrying fluid from said inlet portion;
wherein said bulkhead includes one or more fluid flow paths for providing a fluid path from said one or more fluid channels of said manifold and said reservoir, and wherein said inlet portion and said one or more fluid channels of said manifold together with said one or more fluid flow paths of said bulkhead comprise said means for providing fluid flow;
means for providing fluid flow from said refill port to said reservoir comprising said inlet portion and said one or more fluid channels of said manifold together with said one or more fluid flow paths of said bulkhead;
a flow regulator in fluid communication with said reservoir; and
an outlet port connected to said flow regulator.

18. A method of making a medication delivery device comprising:
providing a cover;

connecting a bulkhead to said cover, said bulkhead including a base portion and a reservoir refill port extending at least partially through said cover, said refill port including:
- a hollow neck portion having first and second open ends,
- a resealable septum within said hollow neck portion near said first end thereof,
- a filter within said hollow neck portion near said second end thereof, and
- a refill port chamber lying between said septum and said filter;

mounting a reservoir between said cover and said bulkhead, said reservoir having a top portion, a side portion, an aperture and a bottom portion;

connecting said bottom portion of said reservoir to said base portion of said bulkhead such that said refill port is positioned laterally adjacent to said reservoir and extends through said aperture in said reservoir;

connecting a manifold to said base portion of said bulkhead, said manifold including an inlet portion for receiving medication passing through said filter and one or more fluid channels for carrying fluid from said inlet portion;

wherein said bulkhead includes one or more fluid flow paths for providing a fluid path from said one or more fluid channels of said manifold and said reservoir;

connecting, between said reservoir and said refill port, a means for providing fluid flow from said refill port to said reservoir, said means for providing fluid flow comprising said inlet portion and said one or more fluid channels of said manifold together with said one or more fluid flow paths of said bulkhead;

connecting a flow regulator in fluid communication with said reservoir; and connecting an outlet port to said flow regulator.

* * * * *